US012653831B2

(12) United States Patent
Sigel et al.

(10) Patent No.: US 12,653,831 B2
(45) Date of Patent: Jun. 16, 2026

(54) METHODS FOR THE NON-TOXIC TREATMENT FOR OPIOID DRUG WITHDRAWAL COMBINING NORIBOGAINE AND CANNABINOIDS

(71) Applicant: DEMERX, INC., Miami, FL (US)

(72) Inventors: Philip Sigel, Coral Gables, FL (US); Deborah Mash, Coral Gables, FL (US); Pascal Goldschmidt, Miami, FL (US)

(73) Assignee: DemeRx, Inc., Miami, FL (US)

( * ) Notice: Subject to any disclaimer, the term of this patent is extended or adjusted under 35 U.S.C. 154(b) by 889 days.

(21) Appl. No.: 17/627,366

(22) PCT Filed: Jul. 13, 2020

(86) PCT No.: PCT/US2020/041789
§ 371 (c)(1),
(2) Date: Jan. 14, 2022

(87) PCT Pub. No.: WO2021/011462
PCT Pub. Date: Jan. 21, 2021

(65) Prior Publication Data

US 2022/0265675 A1 Aug. 25, 2022

Related U.S. Application Data

(60) Provisional application No. 62/874,092, filed on Jul. 15, 2019.

(51) Int. Cl.
*A61K 31/55* (2006.01)
*A61K 31/00* (2006.01)
*A61P 25/36* (2006.01)

(52) U.S. Cl.
CPC ............ *A61K 31/55* (2013.01); *A61K 31/658* (2023.05); *A61P 25/36* (2018.01)

(58) Field of Classification Search
CPC ...... A61K 31/05; A61K 31/352; A61K 31/55; A61P 25/30; A61P 25/36
See application file for complete search history.

(56) References Cited

U.S. PATENT DOCUMENTS

| | | | | |
|---|---|---|---|---|
| 6,348,456 | B1 | 2/2002 | Mash et al. | |
| 8,362,007 | B1 | 1/2013 | Mash et al. | |
| 8,741,891 | B1 | 6/2014 | Mash | |
| 9,345,711 | B2 * | 5/2016 | Friedhoff ............ | A61K 31/407 |
| 9,586,954 | B2 | 3/2017 | Mash | |
| 2005/0203011 | A1 | 9/2005 | Ron | |
| 2012/0253037 | A1 | 10/2012 | Moriarty et al. | |
| 2013/0131046 | A1 | 5/2013 | Moriarty et al. | |
| 2013/0165414 | A1 | 6/2013 | Gless, Jr. et al. | |
| 2013/0165425 | A1 | 6/2013 | Gless, Jr. et al. | |
| 2013/0165647 | A1 | 6/2013 | Moriarty et al. | |
| 2013/0303756 | A1 | 11/2013 | Mash et al. | |
| 2015/0258106 | A1 | 9/2015 | Friedhoff | |

FOREIGN PATENT DOCUMENTS

| | | | |
|---|---|---|---|
| EA | 201591679 | A1 | 5/2016 |
| RU | 2586296 | C2 | 6/2016 |
| WO | WO-2012012764 | A1 | 1/2012 |
| WO | WO-2014144508 | A2 | 9/2014 |
| WO | WO-2017184531 | A1 * | 10/2017 |

OTHER PUBLICATIONS

Hine et. al., Morphine-Dependent Rats: Blockade of Precipitated Abstinence by Tetrahydrocannabinol, Science, 187, 443-445 (Year: 1975).*

Hurd et. al., "Early Phase in the Development of Cannabidiol as a Treatment for Addiction: Opioid Relapse Takes Initial Center Stage", Neurotherapeutica, 12, 807-815 (Year: 2015).*

Combined Search and Examination Report under Section 17 and 18(3), for Application No. GB2300868.3, dated Feb. 3, 2023, 6 pages.

Hurd et al., "Cannabidiol for the Reduction of Cue-Induced Craving and Anxiety in Drug-Abstinent Individuals With Heroin Use Disorder: A Double-Blind Randomized Placebo-Controlled Trial," Am J Psychiatry 2019; 176:911-922; doi: 10.1176/appi.ajp.2019.18101191.

Lamarque et al., "Chronic treatment with $\Delta^9$-tetrahydrocannabinol enhances the locomotor response to amphetamine and heroin. Implications for vulnerability to drug addiction," Neuropharmacology 41 (2001) 118-129.

Morgan et al., "Cannabidiol Attenuates the Appetitive Effects of $\Delta^9$-Tetrahydrocannabinol in Humans Smoking Their Chosen Cannabis," Neuropsychopharmacology (2010) 35:1879-1885.

Prud'Homme et al., "Cannabidiol as an Intervention for Addictive Behaviors: a Systematic Review of the Evidence," Substance Abuse: Research and Treatment 2015:9 33-38 doi: 10.4137/SaRt.S25081.

Wiese et al., "Emerging Evidence for Cannabis' Role in Opioid Use Disorder," Cannabis and Cannabinoid Research vol. 3.1:179-189 (2018).

(Continued)

*Primary Examiner* — Jeffrey H Murray
*Assistant Examiner* — Daniel John Burkett
(74) *Attorney, Agent, or Firm* — COOLEY LLP

(57) ABSTRACT

The present invention is directed to the treatment of chemical substance abuse and withdrawal symptoms, especially withdrawal symptoms associated with opioids, utilizing a combination of an effective amount of a cannabinoid, in particular, cannabidiol (CBD) and/or A9-tetrahydrocannabinol (THC) in combination with low dosage noribogaine or a derivative salt, solvate or ansolvate thereof to treat withdrawal symptoms, both acute and longer term. It has unexpectedly been discovered that the cannabinoids as described herein work in conjunction with noribogaine to synergistically ameliorate and/or attenuate chemical substance abuse, especially including opioid withdrawal symptoms, both acute and longer term symptoms, such that low dose noribogaine (often in daily dosages of 30 milligrams or less) may be favorably co-administered to a patient suffering from withdrawal symptoms, substantially shortening the QT interval of the patient and providing for a particularly safe and effective method to treat opioid withdrawal symptoms.

10 Claims, 1 Drawing Sheet

(56) References Cited

OTHER PUBLICATIONS

Hurd et al., "Early Phase in the Development of Cannabidiol as a Treatment for Addiction: Opioid Relapse Takes Initial Center Stage," Neurotherapeutics, 2015, 12, 807-815.
Valverde, O., et al., "Delta9-tetrahydrocannabinol releases and facilitates the effects of endogenous enkephalins: reduction in morphine withdrawal syndrome without change in rewarding effect", Eur J Neurosci 2001, 13(9), pp. 1816-1824.
Co-pending U.S. Appl. No. 13/593,454, filed Aug. 23, 2012.
Glick, S. D. et al., "Ibogaine-Like Effects of Noribogaine in Rats," Brain Research 713(1-2):294-297 (1996).
Huffman et al., "A Formal Synthesis of (+)-Ibogamine," J. Org. Chem. 50:1460-1464 (1985).
International Search Report and Written Opinion issued by the International Searching Authority for Application No. PCT/US2020/041789, dated Oct. 22, 2020, 9 pages.
Peng et al., "Anxiety-related behavioral responses of pentylenetetrazole-treated zebrafish larvae to light-dark transitions," Pharmacol Biochem Behav. 145:55-65. (Jun. 2016). Epub Mar. 24, 2016.
Back, S.E., & Brady, K.T., "Anxiety disorders with comorbid substance use disorders: diagnostic and treatment considerations," Psychiatric Annals.38(11), 724-729 (Nov. 2008).
Bian, Y. et al. "The development of behavioral sensitization induced by a single morphine exposure in adult zebrafish (*Danio rerio*)," Progress in Neuropsychopharmacology & Biological Psychiatry 113:110456, 11 pages (Month Unknown; Year: 2022). Epub Oct. 15, 2021.
Cachat, J. et al., "Modeling withdrawal syndrome in zebrafish," Behavioural Brain Research 208(2):371-376 (Apr. 2, 2010). Epub Dec. 16, 2009.
Howe, K. et al., "The zebrafish reference genome sequence and its relationship to the human genome," Nature, 496:498-503 (Apr. 25, 2013).
Klee, E. et al., "Zebrafish: a model for the study of addiction genetics," Hum Genet 131:977-1008 (Month Unknown; Year: 2012); Epub Dec. 30, 2011.
Malik, J. A. et al., "Influence of chronic administration of morphine and its withdrawal on the behaviour of zebrafish," Journal of Biosciences, 48:33, 18 pages (Mar. 2023).
Mathur, P. et al., "Use of zebrafish as a model to understand mechanisms of addiction and complex neurobehavioral phenotypes," Neurobiology of Disease 40:66-72 (May 11, 2010). Epub. May 20, 2010.
Miller, S. The ASAM Principles of Addiction Medicine (7th ed.). "Table of Contents," Wolters Kluwer Health (Apr. 8, 2024), 9 pages.
National Institute on Drug Abuse (NIDA), "Why is there comorbidity between substance use disorders and mental illnesses?," (Apr. 2021), 55 pages.

* cited by examiner

Noribogaine (O-desmethylbogaine or 12-hydroxyibogamine)
kappa opioid receptor agonist and mu opioid receptor antagonist
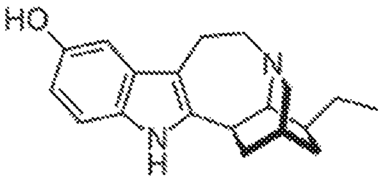
Arachidonylethanolamide
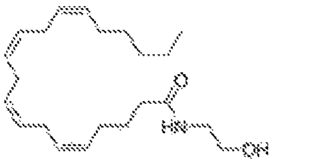
Δ$^9$-tetrahydrocannbinol
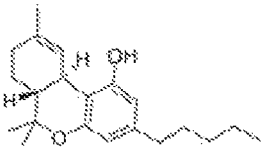
JWH-133
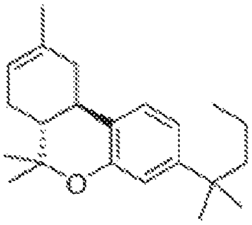
2-arachidonoylglycerol
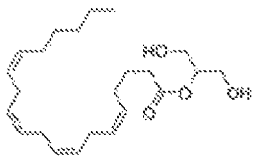
Cannabidiol
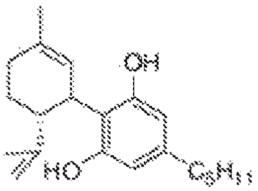
WIN55,212-2
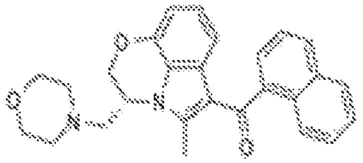
(-)-Δ$^8$-THC
(-)-Δ$^9$-THCV

METHODS FOR THE NON-TOXIC TREATMENT FOR OPIOID DRUG WITHDRAWAL COMBINING NORIBOGAINE AND CANNABINOIDS

CROSS-REFERENCE TO RELATED APPLICATIONS

This application is a U.S. National Stage Application under 35 U.S.C. § 371 of International Application No. PCT/US2020/041789, filed Jul. 13, 2020, which claims priority to U.S. Provisional Application No. 62/874,092, filed on Jul. 15, 2019, each of which is hereby incorporated by reference into this application in its entirety.

FIELD OF THE INVENTION

The present invention is directed to the treatment of chemical substance abuse and withdrawal symptoms, especially withdrawal symptoms associated with opioids, utilizing a combination of an effective amount of a cannabinoid, in particular embodiments, cannabidiol (CBD) and/or Δ9-tetrahydrocannabinol (THC) in combination with low dosage noribogaine or a derivative salt, solvate or ansolvate thereof to treat withdrawal symptoms, both acute and longer term. It has unexpectedly been discovered that the cannabinoids as described herein work in conjunction with noribogaine to synergistically ameliorate and/or attenuate chemical substance abuse, especially including opioid withdrawal symptoms, both acute and longer term symptoms, such that low dose noribogaine (often in daily dosages of 30 milligrams or less) may be favorably co-administered to a patient suffering from withdrawal symptoms, substantially not affecting the QT interval of the patient and providing for a particularly safe and effective method to treat opioid withdrawal symptoms. Methods of treating withdrawal symptoms and decreasing tolerance to opioid analgesic therapy as well as pharmaceutical compositions useful in that treatment are described herein.

BACKGROUND AND OVERVIEW OF THE INVENTION

A remarkable amount of literature has been generated demonstrating the functional similarities between the endogenous opioid and cannabinoid systems. Anatomical, biochemical and molecular data support the existence of reciprocal interactions between these two systems related to several pharmacological responses including reward, cognitive effects, and the development of increased tolerance and dependence. However, the assessment of the bidirectionality of these effects has been difficult due to their variety and complexity, and consequently no clear bidirectionality has been shown. Reciprocal interactions have been well established for the development of physical dependence. Cross-tolerance and cross-sensitization, although not always bidirectional, are also supported by a number of evidence, while less data have been gathered regarding the relationship of these systems in cognition and emotion. Nevertheless, the most recent advances in cannabinoid-opioid cross-modulation have been made in the area of drug craving and relapse processes. Recent focus has been on developments in the cannabinoid-opioid cross-modulation of their behavioral effects and the possible neurobiological substrates involved.

There is presently an epidemic of opioid overdoses associated with the use of illicit drugs such as heroin and related opioids and the misuse of prescribed opioid narcotic pain medications, causing a massacre of human lives and much misery within the population of addicted humans every year, because even a small dose mistake can be fatal when dose escalation in response to drug tolerance exceeds the therapeutic window of these opioid drugs. Chronic use of opioids, even when under medical supervision, is associated with the development of tolerance and escalating risk of withdrawal, both acute and longer-term (e.g., post-acute). The opioid withdrawal syndrome is a serious medical problem that becomes a major reason why addicts keep using opioid drugs. Currently the only treatments to prevent the withdrawal syndrome are either continuing to take opioids (including substitution drugs such as methadone) or symptomatic management of the many severe problems which occur during withdrawal such as diarrhea, vomiting, dehydration, cramping, muscle pain, insomnia, irritability, and anxiety. Addicted individuals often prefer to continue the drugs rather than face the fear of withdrawal. While the sudden reduction in mu opioid receptor activation is the proximal cause of withdrawal, surprisingly little is known about how downstream physiological processes contribute to the syndrome. The subject in the state of withdrawal has many attributes of a severe inflammatory state. Thus, evidence is accumulating that both opioid tolerance and especially acute opioid withdrawal produce a neuroinflammatory state that is a major contributor to the symptoms experienced. Pursuant to the present invention, the inventors propose the hypothesis that glial cells, including microglia, the resident immune cells in the brain, become activated during opioid withdrawal and that the inflammatory cascades mediated by glia-neuron interactions lead to much of the withdrawal syndrome, which can be treated utilizing a combination of noribogaine and at least one cannabinoid compound, especially in preferred embodiments cannabidiol and/or $\Delta^9$-tetrahydrocannabinol.

Opioid addiction is a chronic, progressive disorder that has led to an epidemic of deaths due to overdose, and, as for all chronic illnesses, the therapeutic strategy will require more than one drug to attain therapeutic success. Furthermore, the severity of the opioid withdrawal syndrome is a major disincentive for individuals to attempt to stop opioid use. Therefore, developing new methods of mitigating the opioid withdrawal syndrome will not only alleviate these severe symptoms but may assist addicts in making the decision to discontinue opioid abuse.

Withdrawal from opioid dependence is characterized by traumatic physiologic symptoms, including tremor, anxiety, fever and chills, nausea, vomiting, increased pulse and blood pressure, muscle tension, and diarrhea. The first stage of physiological withdrawal is the acute stage, which usually lasts for days to a week.

The second stage of opioid withdrawal is the post acute withdrawal syndrome (PAWS). During this stage there are fewer physical symptoms, but more emotional and psychological withdrawal symptoms emerge which include intense craving and desire to use drugs to alleviate the psychic pain associated with this stage of withdrawal.

Whether prescription opioids or heroin are abused, these drugs can lead to a post-acute withdrawal syndrome if they are not discontinued slowly and properly based a person's opioid exposure history. People who experience the full intensity of acute withdrawal are more at risk to develop PAWS, which includes cravings, exhaustion, and cognitive impairment that can last for protracted time period up to a year or longer. These people are at increased risk for relapse to opioid abuse after periods of opioid abstinence.

Ibogaine has been used as a method for detoxification from opioids and heroin. Ibogaine was isolated from the roots of tabenanthe iboga for over 100 years and marketed in France in low dose 8 mg tablets under the tradename Lamberene. While anecdotal evidence supports the effectiveness of ibogaine for blocking acute withdrawal in people seeking to detoxify from opioids, no double blind, placebo-controlled trials supported the efficacy of ibogaine as a treatment for addiction or withdrawal.

Noribogaine is an active metabolite of ibogaine. U.S. Pat. No. 6,348,456 discloses highly purified noribogaine and teaches that it should provide dosages from about 0.01 to about 100 mg per kg body weight per day. Noribogaine is a remarkable drug, not only in terms of controlling the dreadful physiological and psychological consequences of opioid withdrawal, but also in reducing the chances of relapse following withdrawal.

During preclinical toxicity studies in various animal models, it was discovered that high doses of noribogaine may cause serious cardiac and CNS adverse effects. More recently, scientists at DemeRx, Inc evaluated pharmacokinetics and metabolism of noribogaine and demonstrated a dose-dependent effect on the EKG QTc interval, as a dose of 30 mg daily shortens the QTc interval, whereas higher doses (above 60 mg/day) increase QTc, the likely culprit for severe cardiac complications seen with high doses of noribogaine. Hence, there is an opportunity to combine noribogaine with other drugs that are synergistic in their ability to ameliorate opioid withdrawal symptoms, thus enhancing the benefit of lower doses of noribogaine, while preventing any significant deleterious clinical complications.

Instructively, the endocannabinoid and opioid systems are known to interact in many different ways, from the distribution of their receptors to cross-sensitization of their behavioral pharmacology. However, the effects of endogenous and exogenous cannabinoids in opioid withdrawal are somewhat paradoxical with studies suggesting that endogenous cannabinoids seem to have no role in somatic withdrawal symptoms, while other studies demonstrate that CBI receptor agonists may alleviate some withdrawal related behaviors in rodent models.

Cannabidiol (CBD) is a major cannabinoid constituent of most *Cannabis* species (*Cannabis saliva*). Unlike THC, cannabidiol binds very weakly to CB1 and CB2 receptors. CBD does not induce psychoactive or cognitive effects and is well tolerated without side effects in humans, thus making it a putative therapeutic target.

In the Central Nervous System, endocannabinoids modulate synaptic function by binding to CB1 and CB2 receptors where they act as a homeostatic mechanism on the neuro-immune axis. In addition to CB1, CB2 receptors are constitutively expressed in microglia cells and its expression increases in inflammatory conditions which occur during opioid withdrawal. Since exogenous cannabinoids can also modulate microglia activation during opioid withdrawal, combinations of use of noribogaine and cannabinoids have unexpected synergistic activity when given to patients undergoing opioid detoxification.

BRIEF DESCRIPTION OF THE INVENTION

In embodiments, the present invention provides a method to co-administer noribogaine with cannabinoid products to a human patient addicted to chemical substances such as opiates and opioids, prescription medicines, such as pain pills, stimulants, anxiety pills, hallucinogens and inhalants, especially prescription opioids, in dosages that provide higher efficacy, and without leading to any significant deleterious clinical consequences. The methods may be used to treat chemical substance abuse and/or to treat withdrawal symptoms associated with chemical substance abuse, especially including withdrawal, which occurs as a consequence of opioid abuse/dependence.

For example, the present invention provides a method of using tetrahydrocannabinoid (THC) and cannabidiol (CBD) compounds, among others in the treatment of chemical substance abuse and withdrawal, especially opioid withdrawal and opioid use disorder. The invention provides methods of alleviating withdrawal symptoms of substance abuse, such as an opioid use disorder in a patient (e.g. a human) suffering from, or predisposed to developing, the disorder, by administering a cannabinoid composition that contains a cannabinoid or cannabinoid derivatives and a pharmaceutically acceptable carrier, additive and/or excipient in combination with noribogaine. The cannabinoid is, for example, delta-9-tetrahydrocannabinol (THC), cannabidiol, cannabinoid or cannabinoid derivatives administered in a non-psychotropic dosage for the patient combined with a dosage of noribogaine. The cannabinoid may be a phytocannabinoid (i.e., obtained from a plant such as *Cannabis* sp. from which the cannabinoid may be extracted and isolated), an endocannabinoid (endogenous cannabinoid) such as arachidonylethanolamide, 2-arachidonoylglycerol (2-AG), among others, or a synthetic cannabinoid, such as JWH-133 or WIN55,212-2, among others (See FIG. 1). The cannabinoid(s) and noribogaine may be administered together in a single pharmaceutical composition dosage form (taken per-os-PO-capsule or as skin patch for examples or separately as co-administered bioactive agents.

In accordance with its broadest aspect, the present invention provides the use of a cannabinoid (e.g. Cannabidiol (CBD) or tetrahydrocannabinol (THC)) compound for the preparation of a pharmaceutical composition with noribogaine for treating or reducing the likelihood of at least one fundamental or more withdrawal signs and symptoms of the withdrawal syndrome, whether during the acute or post-acute phase following opioid abstinence or other chemical substance abstinence syndrome.

In embodiments, the present invention provides an extended-release formulation of noribogaine that has good efficacy and tolerability and acts through a dosing schedule (preferably once or twice a day, up to four times a day) that allows a high level of patient compliance (the skin patch can be administered to patients who are nauseous or refuse PO-intake) when combined with lipid formulations of cannabinoids that have increased bioavailability. In addition to high levels of patient compliance, the present invention provides an effective level of noribogaine for treating and/or reducing the likelihood of withdrawal symptoms while maintaining a safe QTc interval (and never longer than a corrected QT interval (QTc) of >500 ms or an increase in the QTc of >60 ms while providing an anti-inflammatory cannabinoid effect, which is mediated through microglia processes, thus providing for a synergistic effect on opioid analgesic withdrawal.

In an alternative embodiment, the present invention also provides a method for treating withdrawal symptoms in a patient in a dosage of noribogaine that provides favorable pharmacokinetics including a Cmax of noribogaine of less than 120 ng/ml in serum and AUC/24 of about 400 ng/ml.

In embodiments, the patient is administered a dosage of noribogaine of 60 mg or less, preferably 30 mg or less at intervals of 24 hours and combined with oral (or patch) dosage forms of cannabinoids, between 0.5 mg to 1,000 mg or more, often 62.5 mg to 1,000 mg (titrated for each patient to optimize benefits and minimize side effects, see Table). THC is often used in combination with noribogaine, generally at a non-psychotropic concentration (THC less than 0.3%). Combining CBD and low dose of THC (<0.3%, see Table) has been shown to potentiate the benefits of CBD. Both cannabinoids appear to potentiate the benefits of noribogaine. Some patients, especially those who use not only opioids, but also recreational THC (recreational "pot-smokers" for example), may require a higher dose of THC to withdraw from opioids, and avoid relapses (for example, in this embodiment, daily dose of THC: 62.5 mg to 250 mg, with or without CBD, see Table).

In embodiments, the methods according to the present invention include the following dose ranges for noribogaine in combination with cannabinoid actives. Noribogaine is generally used at a daily dosage of 8 mg to 60 mg, often 30 mg, except for patients with borderline QTc (449 ms), who will be started on a dose of 8-10 mg and increased to 30 mg under continued telemetry to assess impact on rate corrected QTc (increased or reduced). THC, when used, is preferably used in a daily dose of between 62.5 mg and 250 mg (see table). Other cannabinoid derivatives as described herein are generally used within the same daily dosage ranges as for THC, depending upon the psychotropic activity that these derivatives display when administered to a patient. It is preferable to limit or avoid psychotropic activity unless the psychotropic activity of the cannabinoid is beneficial to treatment, for example, in instances of co-morbidity, or prior heavy use of such.

Accordingly, the present invention is directed to methods for treating chemical substance abuse including opioid withdrawal symptoms or patients who are suffering from opioid withdrawal symptoms in either the acute phase or post-acute phase of the withdrawal syndrome, for inhibiting or attenuating opioid withdrawal symptoms in patients who are anticipating or are commencing cessation of opioid analgesic therapy. In alternative embodiments, the present methods may be used for decreasing the tolerance of a patient to opioid analgesic therapy and allowing a longer period of opioid analgesic therapy before. It has been discovered that co-administration of a cannabinoid as described herein, especially (−)-cannabidiol and/or $\Delta^9$-tetrahydrocannabinol (THC), among others, as described herein, in combination with low dose noribogaine provides an effective therapy for chemical substance and especially opioid withdrawal, both acute and longer-term (post-acute withdrawal), which synergistically enhances withdrawal therapy and separately, decreases opioid tolerance such that opioids may be given at lower doses for longer periods of time before tolerance and withdrawal occur. Thusly, the present invention makes use of noribogaine in a daily dose of between 8-10 mg and 60 mg, in combination with at least one cannabinoid, often CBD and/or THC in amounts which are preferably non-psychotrophic, ranging from 0.5 mg to 1,000 mg, often 62.5 to 1,000 mg. In embodiments, the daily dose of cannabidiol may be elected to approximately 1.0 mg to 1,000 mg, often 62.5-250 mg. or more, depending on the patient's response to the agent.

In embodiments, the invention is directed to pharmaceutical compositions comprising an effective amount of noribogaine or a pharmaceutically acceptable salt or ansolvate thereof, in combination with at least one cannabinoid compound or a pharmaceutically acceptable salt or ansolvate thereof, optionally, and most often in combination with a pharmaceutically acceptable carrier, additive or excipient. The pharmaceutical compositions according to the present invention are typically formulated in oral or skin patch dosage form, including using sustained release approaches for delivering compounds over longer periods of time and enhancing the bioavailability of the noribogaine and cannabinoid. The amount of noribogaine included in said compositions ranges from 8 mg to 60 mg, often 8-10 mg to 30 mg. and the amount of cannabinoid included in said compositions ranges from 0.5 mg to 1,000 mg, often 1 mg to 800 mg, more often 1 to 250 mg or 62.5 to 250 mg.

These and/or other embodiments of the present invention may be readily gleaned from the detailed description of the invention which follows.

BRIEF DESCRIPTION OF THE FIGURES

FIG. 1 shows the chemical structure of noribogaine and certain cannabinoids which find use in the present invention.

DETAILED DESCRIPTION OF THE INVENTION

Unless defined otherwise, all technical and scientific terms used herein have the same meaning as commonly understood by one of ordinary skill in the art to which this invention belongs. As used herein the following terms have the following meanings.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a human, to whom treatment, including prophylactic treatment (prophylaxis), with the compounds or compositions according to the present invention is provided. For treatment of those conditions or disease states which are specific for a specific animal such as a human patient, the term patient refers to that specific animal. In most instances, the patient or subject of the present invention is a human patient of either or both genders, but may include a domesticated animal or a laboratory animal.

The "about" when used before a numerical designation, e.g., temperature, time, amount, concentration, and such other, including a range, indicates approximations which may vary by (+) or (−) 20%, 10%, 5% or 1%, or any subrange or subvalue there between. Preferably, the term "about" when used with regard to a dose amount means that the dose may vary by +/−20%. For example, "about 2 mg/kg noribogaine" indicates that a patient may be administered a dose of noribogaine between 1.6 mg/kg and 2.4 mg/kg. In another example, about 30 mg per unit dose of noribogaine indicates that the unit dose may range from 24.6 mg to 36 mg.

"Administration" refers to introducing an agent, such as noribogaine, into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent, such as noribogaine, may be administered by direct blood stream delivery, e.g. sublingual, buccal, intranasal, or intrapulmonary administration. Oral and/or topical/transdermal delivery may be preferred, depending on the embodiment.

The term "coadministration" shall mean that at least two compounds or compositions (i.e., noribogaine and at least one cannabinoid) are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Compounds according to the present invention may be administered with one or more additional bioactive agents, especially including an additional antibiotic for purposes of treating bacterial, especially gram negative bacteria.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of an agent, such as, noribogaine, noribogaine derivative, or salt and/or solvate thereof one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "effective" is used herein, unless otherwise indicated, to describe an amount of a compound or component which, when used within the context of its use, produces or effects an intended result, whether that result relates to the prophylaxis and/or therapy of an infection and/or disease state, especially a bacterial infection including a infection within the context of its use or as otherwise described herein. The term effective subsumes all other effective amount or effective concentration terms (including the term "therapeutically effective") which are otherwise described or used in the present application.

The term "therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of noribogaine, in the context of treating drug withdrawal, refers to an amount of noribogaine that attenuates the dependency and/or symptoms of acute withdrawal for at least 2 hours beyond control (placebo), at least 5 hours beyond control, and preferably at least 10 hours beyond control. Within the context of decreasing opioid tolerance, therapeutically effective amount refers to an amount of noribogaine that decreases the tolerance to opioid analgesic therapeutic activity by at least two hours beyond control (placebo), at least 5 hours beyond control, at least 12 hours beyond control and often 24 hours or longer beyond control.

The term "compound" is used herein to describe any specific compound or bioactive agent disclosed herein, including any and all stereoisomers (including diastereomers, individual optical isomers/enantiomers or racemic mixtures and geometric isomers), pharmaceutically acceptable salts, ansolvates and prodrug forms. The term compound herein refers to stable compounds. Within its use in context, the term compound may refer to a single compound or a mixture of compounds as otherwise described herein. This invention is not limited to any particular chemical form of noribogaine or noribogaine derivative, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

The term "Noribogaine" refers to the compound:

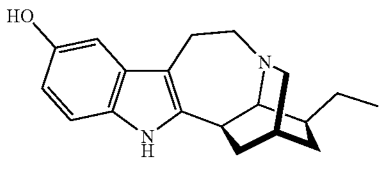

as well as noribogaine derivatives or pharmaceutically acceptable salts and pharmaceutically acceptable solvates thereof. It should be understood that where "noribogaine" is mentioned herein, one more polymorphs of noribogaine can be utilized and are contemplated. In some embodiments, noribogaine is noribogaine glucuronide. Noribogaine can be prepared by demethylation of naturally occurring ibogaine, which is isolated from Tabernanth iboga, a shrub of West Africa. Demethylation may be accomplished by conventional techniques such as by reaction with boron tribromide/methylene chloride at room temperature followed by conventional purification. See, for example, Huffman, et al., J. Org. Chem. 50:1460 (1985), which is incorporated herein by reference in its entirety. Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

The term "noribogaine derivatives" refer to, without limitation, esters or O-carbamates of noribogaine, or pharmaceutically acceptable salts and/or solvates of each thereof. Also encompassed within this invention are derivatives of noribogaine that act as prodrug forms of noribogaine. A prodrug is a pharmacological substance administered in an inactive significantly less active) form. Once administered, the prodrug is metabolized in vivo into an active metabolite. Noribogaine derivatives include, without limitation, those compounds set forth in U.S. Pat. Nos. 6,348,456 and 8,362,007; as well as in U.S. patent application Ser. No. 13/165,626; and US Patent Application Publication Nos. US2013/0131046; US2013/0165647; US2013/0165425; and US2013/0165414; all of which are incorporated herein by reference. Non-limiting examples of noribogaine derivatives encompassed by this invention are given in more detail in the "Compositions" section below.

In some embodiments, the methods of the present invention entail the administration of a prodrug of noribogaine that provides the desired maximum serum concentrations and efficacious average noribogaine serum levels. A prodrug of noribogaine refers to a compound that metabolizes, in vivo, to noribogaine. In some embodiments, the prodrug is selected to be readily cleavable either by a cleavable linking arm or by cleavage of the prodrug entity that hinds to noribogaine such that noribogaine is generated in vivo. In one preferred embodiment, the prodrug moiety is selected to facilitate binding to the μ, and/or κ receptors in the brain either by facilitating passage across the blood brain barrier or by targeting brain receptors other than the μ and/or κ receptors. Examples of prodrugs of noribogaine are provided in U.S. patent application Ser. No. 13/165,626, the entire contents of which are incorporated herein by reference.

This invention is not limited to any particular chemical form of noribogaine or noribogaine derivative, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

The term "cannabinoid" is used to describe any number of diverse compounds that acts on a cannabinoid receptor (cannabinoid receptor type I and cannabinoid receptor type II). Cannabinoids are generally described as phytocannabinoids (derived from plants, especially *Cannabis* sp. plants), endocannabinoids (endogenous to a biological system) or synthetic cannabinoids. The term cannabinoid embraces non-salt forms, pharmaceutically acceptable salt forms, solvates or ansolvates thereof.

Phytocannabinoids are generally described as cannabis-derived cannabinoids and non-cannabis derived cannabinoids. At least 113 cannabinoid compounds have been isolated from the *Cannabis* plant and the most important cannibinoids compounds within this series are tetrahydrocannabinol (THC), cannabidiol (CBD) and cannabinol (CBN). Exemplary cannabinoids include, for example $\Delta^9$-tetrahydrocannabinol ($\Delta^9$THC), $\Delta^8$-tetrahydrocannabinol ($\Delta^8$THC), cannabidiol (CBD), cannabinol (CBN), tetrahydrocannabinolic acid (THCA), cannabidiolic acid (CBDA), cannabigeol (CBG), cannabichromene (CBC), cannabicyclol (CBL), cannabivarin (CBV), tetrahydrocannabivarin (THCV), cannahidivarin (CBDV), cannabigerovarin (CBGV), cannabichromevarin (CBCV), cannabigerovarin (CBGV), cannabigerol monomethyl ether (CBGM), cannbielsoin (CBE), cannabicitran (CBT), among others. Non-cannabis phytocannabinoids include the lipophilic alkamides (alkylamides) from *Echinachea* species, especially the cis/trans isomers dodeca-2E4E,8Z,10E/Z-tetraenoic-acid-isobutylamide.

Endocannahinoids are generally described as substances produced from within the body that activate the cannabinoid receptors. These compounds include, for example, Anandamide, 2-Arachidonoylglycerol (2-AG), Arachidonylethanolamide, noladin ether, virodhamine and N-arachidonyl dopamine (NADA), among others.

Synthetic cannabinoids are generally described as non-natural substances which are modulators of cannabinoid receptors which have been chemically synthesized based upon combinatorial chemistry or other approaches for identifying active compounds such as structure activity relationships. These synthetic cannabinoids are not found in nature. Exemplary synthetic cannabinoids include JWH-133, WIN-55,212-2, JWH-007, JWH-018, JWH-073, JWH-200, JWH-250, JWH-398, AM-1221, AM-2201, AM-694, RCS-8, CP-47,947, CP-55,940, UR-144, XLR-11, 5F-AKB-48, APICA, STS-135, AB-PINACA, AB-FUBINACA, PB-22 and 5F-PB-22, among others.

Although the cannabinoids all show activity and are useful in the present invention, preferred cannabinoids are those which show enhanced anti-inflammatory activity and/or suppress various forms of discomfort Preferred cannabinoids include THC and/or CBD).

The term "pharmaceutically acceptable" as used herein means that the compound or composition is suitable for administration to a subject to achieve the treatments described herein, without unduly deleterious side effects in light of the severity of the disease and necessity of the treatment.

The term "independently" is used herein to indicate that the variable, which is independently applied, varies independently from application to application.

The terms "treat", "treating", and "treatment", etc., as used herein within context, also refers to any action providing a benefit to a patient at risk for or suffering from chemical substance withdrawal, especially opioid withdrawal which can be treated pursuant to the present invention (e.g., inhibit, reduce the severity, cure, etc.). Treatment, as used herein, principally encompasses therapeutic treatment, but may also encompass both prophylactic and therapeutic treatment, depending on the context of the treatment (for example in anticipation of the cessation of a chemical substance and/or opioid therapy with an expectation that withdrawal symptoms will likely occur). The term "prophylactic" when used in context, means to reduce the likelihood of an occurrence or in some cases, reduce the severity of an occurrence within the context of the treatment of a disease state or condition otherwise described herein.

The term "prevention" is used within context to mean "reducing the likelihood" of a condition or disease state from occurring as a consequence of administration or concurrent administration of one or more compounds or compositions according to the present invention, alone or in combination with another agent. Thus, the term prevention is used within the context of a qualitative measure and it is understood that the use of a compound according to the present invention to reduce the likelihood of an occurrence of a condition or disease state as otherwise described herein will not be absolute, but will reflect the ability of the compound to reduce the likelihood of the occurrence within a population of patients or subjects in need of such prevention.

The therapeutically effective amount of the compound may be higher or lower, depending on the route of administration used. For example, when direct blood administration (e.g., sublingual, pulmonary and intranasal delivery) is used, a lower dose of the compound may be administered. In one aspect, a therapeutically effective amount of noribogaine or derivative is from about 0.1 mg to less than 0.4 mg. per kg of body weight with the dose not to exceed 30 mg of noribogaine in a 24 hour period. In other embodiments, up to 60 mg of noribogaine is administered to the subject or patient within a 24 hour period. In the case of cannabinoids, the daily effective amount ranges from less than about 0.01 mg. to about 14 mg. per kg of body weight. Where other routes of administration are used, a higher dose of the compound may be administered.

A "low dose level" of a drug is an amount of noribogaine, noribogaine derivative, or pharmaceutical salt and/or solvate thereof that is sufficient to treat drug addiction or to treat, prevent, or attenuate acute withdrawal symptoms, but not high enough to pose any significant risk to the patient and is typically substantially less than the dosage used in conventional noribogaine therapy. This amount is often less than 30 mg, often between 8 and 30 mg. Therapeutic levels of drugs can be determined by tests that measure the actual concentration of the compound in the blood of the patient. This concentration is referred to as the "serum concentration." Where the serum concentration of noribogaine is mentioned, it is to be understood that the term "noribogaine" encompasses any form of noribogaine, including derivatives thereof.

A "sub-therapeutic level" of noribogaine or pharmaceutical salt and/or solvate thereof that is less than the therapeutic level described above. For example, the sub-therapeutic level of noribogaine may be e.g., 80%, 70%, 60%, 50%, 40%, 30%, 20%, or 10% less than a therapeutically effective amount (e.g., between 8 and 60 mg, often 10 and 30 mg) of noribogaine, or any subvalue or subrange there between. Sub-therapeutic levels of noribogaine may coincide with "maintenance amounts" of noribogaine which are amounts, less than the therapeutically effective amount, that provide some attenuation and/or prevention of post-acute withdrawal syndrome in a patient. The maintenance amount of the compound is expected to be less than the therapeutically effective amount.

As defined herein, a "prophylactical effective amount" of a drug or agent is an amount, typically less than the therapeutically effective amount, that provides inhibition, attenuation and/or prevention of a disease or disorder or symptoms of a disease or disorder in a patient. For example, the prophylactically effective amount of the compound is expected to be less than the therapeutically effective amount because the level of inhibition does not need to be as high in a patient who no longer has a disease or disorder or symptoms of a disease or disorder (e.g., no longer physically addicted to nicotine). For example, a prophylactically effective amount is preferably 90%, 80%, 70%, 60%, 50%, 40%, 30%, 20%, or 10% less than a therapeutically effective amount. However, a prophylactically effective amount may be the same as the therapeutically effective amount, for example when a patient who is physically addicted to nicotine is administered noribogaine to attenuate cravings for a period of time.

As defined herein, a "maintenance amount" of a drug is an amount, typically less than the therapeutically effective amount that provides attenuation and/or prevention of post-acute withdrawal syndrome in a patient. The maintenance amount of the compound is expected to be less than the therapeutically effective amount because the level of inhibition does not need to be as high in a patient who is no longer physically addicted to the addictive substance or drug. For example, a maintenance amount is preferably 90%, 80%, 70%, 60%, 50%, 40%, 30%, 20%, or 10% less than a therapeutically effective amount, or any subvalue or subrange there between.

As used herein, the term "QT interval" refers to the measure of the time between the start of the Q wave and the end of the T wave in the electrical cycle of the heart. Prolongation of the QT interval refers to an increase in the QT interval and depending on level of the QT interval, can signify cardiovascular risk (e.g. tachycardia, ventricular tachyarrhythmias, sudden death, etc). In embodiments, the QT interval of patients administered compounds according to the present invention is less than 50 ms, less than 40 ms, less than 30 ms and in certain embodiments, less than 20 ms. The QTc represents a correction of the QT interval, with the purpose of allowing interpretation of QT size, in spite of heart rate variability. The standard formula to calculate QTc is the Bazett's correction ($QTc=QT/RR^{0.50}$), where RR represents the length of the preceding R to R interval.

The terms "addiction", "abuse", and "dependence" are used interchangeably to refer to the patient's inability to stop using the addictive substance, even when it would be in his/her best interest to stop. A patient may be physically and/or behaviorally addicted to a substance, principally because of the inability to deal with the withdrawl symptoms that occur during acute or post-acute withdrawal. The DSMIV-TR criteria for dependency include: Dependence or significant impairment or distress, as manifested by 3 or more of the following during a 12 month period:

1. Tolerance or markedly increased amounts of the substance to achieve intoxication or desired effect or markedly diminished effect with continued use of the same amount of substance;
2. Withdrawal symptoms or the use of certain substances to avoid withdrawal symptoms;
3. Use of a substance in larger amounts or over a longer period than was intended;
4. Persistent desire or unsuccessful efforts to cut down or control substance use;
5. Involvement in chronic behavior to obtain the substance, use the substance, or recover from its effects;
6. Reduction or abandonment of social, occupational or recreational activities because of substance use;

7. Use of substances even though there is a persistent or recurrent physical or psychological problem that is likely to have been caused or exacerbated by the substance.

The term "chemical substance that may cause substance abuse" is used to describe a chemical substance which can produce addiction, abuse or dependence, and often induces withdrawal symptoms after abstinence. These substances include opiates and opioids, prescription medicines, such as pain pills, stimulants, anxiety pills, hallucinogens and inhalants. Particular chemical substances that may cause substance abuse in patients or subjects include, for example, opiates such as morphine, codeine, thebaine, heroin, nicomorphine, dipropanoylmorphine, desomorphine, methyldesorphine, acetylpropionylmorphine, dibenzoylmorphine, diacetyldihydromorphine, among others, alcohol, prescription medicines including pain pills, stimulants and anxiety pills, nicotine and sleeping pills including opioids (synthetic or semi-synthetic opiates) and other agents such as tramadol, oxycontin, hydrocodone, hydromorphone, tapentadol, meperidine, buprenorphine, fentanyl, methadone, codeine, diclofenac, ketorolac, etodolac, pregabalin, acetaminophen, ibuprofen, naproxen, celecoxib, hydroxyzine, lidocaine, amytriptylene, nortriptyline, duloxetine, clonidine, benzodiazepines, including diazepam and clonazepam, amphetamine, caffeine, ephedrine, MDMA, DMT, PCP, mephedrone, methamphetamine, methylphenidate, cocaine, nicotine, phenylpropanolamine, propylhexedrine, pseudoephedrine, *Catha edulis* (Khat) and alprazolam (Xanax), aerosol products, cleaning agents, solvents and adhesives, among others.

The term "dose" refers to a range of noribogaine, noribogaine derivative, or pharmaceutical salt or solvate thereof or a cannabinoid that provides a therapeutic serum level of noribogaine when given to a patient in need thereof. The dose is recited in a range, for example from 8 to 60 (often 10 to 30) mg in the case of noribogaine or from 0.5 mg to 1 grain (often 1 mg to 800 mg, often 62.5 mg to 250 mg or more) for a cannabinoid, and can be expressed either as milligrams or as mg/kg body weight. The attending clinician will select an appropriate dose from the range based on the patient's weight, age, degree of addiction, health, and other relevant factors, all of which are well within the skill of the art.

The term "unit dose" or "unit dosage form" refers to a dose of drug that is given to patient to provide therapeutic results, independent of the weight of the patient. In such an instance, the unit dose is sold in a standard form (e.g., 10, 20, 30, 40, 50 or 60 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

A "pharmaceutically acceptable solvate" or "hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The term "solvate" is taken to mean that a solid-form of a compound that crystallizes with one or more molecules of solvent trapped inside. A few examples of solvents that can be used to create solvates, such as pharmaceutically acceptable solvates, include, but are certainly not limited to, water, methanol, ethanol, isopropanol, butanol, $C_1$-$C_6$ alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the an and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest.

The term "pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like. Pharmaceutically acceptable salts are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids, some of which are described above. Suitable salts include those derived from alkali metals such as potassium and sodium, alkaline earth metals such as calcium, magnesium and ammnonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, the term "salt" shall mean a pharmaceutically acceptable salt, consistent with the use of the compounds as pharmaceutical agents.

As will be apparent to the skilled artisan upon reading this disclosure, this invention provides compositions for treating substance abuse in a subject, comprising noribogaine, noribogaine derivatives, prodrugs of noribogaine, pharmaceutically acceptable salts and/or solvates of each thereof. This invention further provides compositions for treating, attenuating, or preventing withdrawal symptoms in a drug-addicted subject, comprising noribogaine, noribogaine derivatives, prodrugs of noribogaine, pharmaceutically acceptable salts and/or solvates of each thereof.

Pharmaceutical compositions comprise combinations of an effective amount of at least one noribogaine compound disclosed herein, often according to the present invention and one or more cannabinoid compounds as otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin bacterial infections or other diseases which occur in or on the skin. Suitable topical formulations are readily prepared for each of these areas or organs. Topical application for the lower intestinal tract can be effected in a rectal suppository formulation see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.5 milligram to about 750 milligrams or more, more preferably about 1 milligram to about 600 milligrams, and even more preferably about 10 milligrams to about 500 milligrams of active ingredients.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Methods of Treatment

In one embodiment, the present invention is directed to the treatment of acute or post-acute withdrawal from an addictive substance, generally an opioid analgesic, in an addicted patient comprising the administration of a therapeutically effective amount of noribogaine, a noribogaine derivative, pharmaceutically acceptable salt and/or solvate thereof in combination with an effective amount of at least one cannabinoid.

In an embodiment, the present invention is directed to a method for treating or reducing the likelihood of withdrawal in an opioid addicted patient, comprising administering to the patient a dosage of noribogaine, noribogaine derivative, or a pharmaceutically acceptable salt and/or solvate thereof in combination with an effective amount of a cannabinoid compound that provides favorable pharmacokinetics including a Cmax of noribogaine of less than 120 ng/ml in serum and AUC/24 of about (400) ng/ml, said concentration being sufficient to inhibit or ameliorate said withdrawal while maintaining a QT interval of less than about 450 ms during said treatment.

In an embodiment, the present invention is directed to a method for attenuating withdrawal symptoms in a human patient susceptible to such symptoms due to substance addiction, comprising administering to the patient a dosage of noribogaine from about 8 to 60 mg at intervals of about 24 hours and combined with oral dosage forms of cannabinoids of between 0.1 mg to 800 mg or more (up to a gram). THC is often used in combination with noribogaine, generally at a non-psychotropic concentration or a daily dose of between 0.5 mg and 200 mg, often 1 and 200 mg, often 5 and 100 mg, and an amount of cannabidiol (CBD), when used, ranges from 50 mg up to 800 mg. often 100-800 mg, and 400 to 800 mg cannabidiol or pharmaceutically acceptable salt and/or solvate thereof, said concentration of actives (noribgaine and cannabinoid) being sufficient to attenuate said symptoms while maintaining a QT interval of less than about 50 ms during said treatment. In some embodiments, the concentration is sufficient to attenuate said symptoms while maintaining a QT interval of less than about 450 ms during treatment. In preferred embodiments, the concentration is sufficient to attenuate said symptoms while maintaining a QT interval of less than about 30 ms during treatment. In one embodiment, the concentration is sufficient to attenuate said symptoms while maintaining a QT interval of less than about 20 ms during treatment. In one embodiment, the withdrawal symptoms are symptoms of acute withdrawal. In another embodiment, the withdrawal symptoms are symptoms of post-acute withdrawal.

In one aspect, this invention relates to a method for attenuating withdrawal symptoms in a human patient susceptible to such symptoms due to substance addiction, comprising administering to the patient a dosage of noribogaine, noribogaine derivative or pharmaceutically acceptable salt and/or solvate thereof that provides an average serum concentration, of noribogaine, noribogaine derivative, or pharmaceutically acceptable salt and/or solvate thereof in combination with a cannabinoid as described herein that provides an average serum concentration which is sufficient to attenuate said symptoms while maintaining a QT interval of less than about 450 ms during said treatment. In some embodiments, the concentration is sufficient to attenuate said symptoms while maintaining a QT interval of less than about 450 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 450 ms during treatment. In one embodiment, the withdrawal symptoms are symptoms of acute withdrawal. In another embodiment, the withdrawal symptoms are symptoms of post-acute withdrawal.

In one embodiment, the daily dosage of noribogaine, noribogaine derivative, or pharmaceutically acceptable salt and/or solvate thereof is between about 8 mg and about 50 mg., preferably 8 mg and 30 mg, and the daily dosage of cannabinoid or a pharmaceutically acceptable salt thereof is between 0.5 mg and 1 g, more often 1 mg and 800 mg., depending on the cannabinoid combined with noribogaine, noribogaine derivative, or pharmaceutically acceptable salt and/or solvate thereof. In one embodiment, the daily dosage of THC when used ranges from about 0.5 mg to about 250 mg or more (often up to one gram) often 1 mg to about 200 mg. In the case of CBD, the daily dosage of CBD used ranges from 25-50 mg up to 800 mg. often 100-800 mg, and often 400 to 800 mg cannabidiol. In one embodiment, the daily dosage of noribogaine, noribogaine derivative, or pharmaceutically acceptable salt and/or solvate thereof is between about 10 mg and about 30 mg and the daily dosage of cannabinoid ranges from about 0.5 mg. to 1 g, more often 1 mg to 800 mg. In one embodiment, the daily dosage or aggregate dosage of noribogaine, noribogaine derivative, or pharmaceutically acceptable salt and/or solvate thereof is between about 8 mg and about 20 mg. In one embodiment, the daily dosage of noribogaine, noribogaine derivative, or pharmaceutically acceptable salt and/or solvate thereof is between about 10 mg and about 25 mg. The daily dosage may be administered in a single dosage form (for example sustained and/or controlled release) or in subdosages (once, twice, three, four, five or up to six times per day). In some embodiments, the patient is administered an initial dose of noribogaine, noribogaine derivative, or pharmaceutically acceptable salt and/or solvate thereof in combination with at least one cannabinoid followed by one or more additional doses. It is noted that the noribogaine, noribogaine derivative or pharmaceutically acceptable salt and/or solvate thereof may be co-administered with the cannabinoid or pharmaceutically acceptable salt simultaneously, contemporaneously, in seriatim or at varying intervals at different times to maintain therapeutically effective blood concentrations of the agents in the patient. The ranges presented above include both extremes as well as any subrange or subvalue there between.

In some embodiments, the initial or bolus dose of noribogaine, noribogaine derivative, or pharmaceutically acceptable salt and/or solvate thereof is from about 8 mg to about 60 mg, often 10 mg to 50 mg, 15 mg to 40 mg, 20 mg to 30 mg or 25 mg to 30 mg. In one embodiment, the initial dose is about 50 mg. In one embodiment, the initial dose is about 60 mg. In embodiments, the initial dose is 30 mg. In embodiments, the initial dose is 50-60 mg and the following maintenance doses are 30 mg. The initial dose is provided as a bolus dose to rapidly increase the blood concentration of noribogaine, noribogaine derivative, or pharmaceutically acceptable salt and/or solvate thereof before placing the patient on a lower additional dosage regimen or maintenance dose. In the case of cannabinoids or their pharmaceutically acceptable salts, the initial dose may be the same or higher than the additional doses, with the intent of the initial dose to function as a bolus dose to rapidly raise blood concentration of the cannabinoid before administering additional or maintenance doses.

In some embodiments, the one or more additional doses of noribogaine, noribogaine derivative, or pharmaceutically acceptable salt and/or solvate thereof or cannabinoid or a pharmaceutically acceptable salt thereof are lower than the initial dose. In one embodiment, the one or more additional doses are from about 8 mg to about 50 mg, often about 10 mg to 30 mg. In one embodiment, the one or more additional doses may or may not comprise the same amount of noribogaine, noribogaine derivative, or pharmaceutically acceptable salt and/or solvate thereof. In one embodiment, at least one additional dose is at least about 8 mg. In one embodiment, at least one additional dose is about 10 mg. In one embodiment, at least one additional dose is about 15 mg. In one embodiment, at least one additional dose is about 20 mg. In one embodiment, at least one additional dose is about 25 mg. In one embodiment, at least one additional dose is about 30 mg.

In one embodiment, the one or more additional doses are administered periodically, at varying intervals depending on the release characteristics of the dosage forms. In one embodiment, the one or more additional doses are administered approximately every 4 hours. In one embodiment, the one or more additional doses are administered every 6 hours. In one embodiment, the one or more additional doses are administered approximately every 8 hours. In one embodiment, the one or more additional doses are administered approximately every 10 hours. In one embodiment, the one or more additional doses are administered approximately every 12 hours. In one embodiment, the one or more additional doses are administered approximately every 18 hours. In one embodiment, the one or more additional doses are administered approximately every 24 hours. In one embodiment, the one or more additional doses are administered approximately every 36 hours, in one embodiment, the one or more additional doses are administered approximately every 48 hours or longer.

In some embodiments, the patient is administered a higher dose (therapeutic) dose of noribogaine and cannabinoid within the therapeutic range for a period of time to ameliorate the most significant symptoms of withdrawal, and then is administered a lower (maintenance) dose to prevent relapse. In some embodiments, the patient is administered a therapeutic dose of noribogaine, noribogaine derivative, or pharmaceutically acceptable salt and/or solvate thereof and cannabinoid or pharmaceutically acceptable salt thereof for a period of time to ameliorate the most significant symptoms, and then is administered a decreasing (tapered) amount of noribogaine, noribogaine derivative, or pharmaceutically acceptable salt and/or solvate thereof and cannabinoid or a pharmaceutically acceptable salt thereof over time until the maintenance dose is reached.

In some embodiments, the maintenance dose of noribogaine, noribogaine derivative, or pharmaceutically acceptable salt and/or solvate thereof and cannabinoid or pharmaceutically acceptable salt thereof is about 10% to about 80% of the therapeutic dose. In some embodiments, the maintenance dose of noribogaine, noribogaine derivative, or pharmaceutically acceptable salt and/or solvate thereof and cannabinoid or pharmaceutically acceptable salt thereof is about 70% of the therapeutic dose. In some embodiments, the maintenance dose is about 60% of the therapeutic dose. In some embodiments, the maintenance dose is about 50% of the therapeutic dose. In some embodiments, the maintenance dose is about 40% of the therapeutic dose. In some embodiments, the maintenance dose is about 30% of the therapeutic dose. In some embodiments, the maintenance dose is about 20% of the therapeutic dose. In some embodiments, the maintenance dose is about 10% of the therapeutic dose.

In some embodiments, the maintenance average serum level of noribogaine, noribogaine derivative, or pharmaceutically acceptable salt and/or solvate thereof and cannabinoid or pharmaceutically acceptable salt thereof is about 10% to about 80% of the therapeutic average serum level of noribogaine, noribogaine derivative, or pharmaceutically acceptable salt and/or solvate thereof and cannabinoid or pharmaceutically acceptable salt thereof. In some embodiments, the maintenance average serum level of noribogaine, noribogaine derivative, or pharmaceutically acceptable salt and/or solvate thereof and cannabinoid or pharmaceutically acceptable salt thereof is about 70% of the therapeutic average serum level of noribogaine, noribogaine derivative, or pharmaceutically acceptable salt and/or solvate thereof and cannabinoid or pharmaceutically acceptable salt thereof. In some embodiments, the maintenance average serum level of noribogaine, noribogaine derivative, or pharmaceutically acceptable salt and/or solvate thereof and cannabinoid or pharmaceutically acceptable salt thereof is about 60% of the therapeutic average serum level of noribogaine, noribogaine derivative, or pharmaceutically acceptable salt and/or solvate thereof and cannabinoid or pharmaceutically acceptable salt thereof. In some embodiments, the maintenance average serum level of noribogaine, noribogaine derivative, or pharmaceutically acceptable salt and/or solvate thereof and cannabinoid or pharmaceutically acceptable salt thereof is about 10-50% of the therapeutic average serum level of noribogaine, noribogaine derivative, or pharmaceutically acceptable salt and/or solvate thereof and cannabinoid or pharmaceutically acceptable salt thereof.

In some embodiments, the therapeutic dose of noribogaine, noribogaine derivative, or pharmaceutically acceptable salt and/or solvate thereof and cannabinoid or pharmaceutically acceptable salt thereof is a tapered dosing over a period of time, during which the patient is detoxified, for example, without suffering significant acute withdrawal symptoms. Without being bound by theory, it is believed that tapering will allow the full therapeutic effect of the compound with less prolongation or even reduction of the QT interval. Tapering involves administration of one or more subsequently lower doses of the noribogaine and cannabinoid compound over time. For example, in some embodiments, the first tapered dose is about 50% to about 95% of the first or original dose. In some embodiments, the second tapered dose is about 40% to about 90% of the first or original dose. In some embodiments, the third tapered dose is about 30% to about 85% of the first or original dose. In some embodiments, the fourth tapered dose is about 20% to about 80% of the first or original dose. In some embodiments, the fifth tapered dose is about 10% to about 75% of the first or original dose.

In some embodiments, the first tapered dose is given after the first dose of noribogaine, noribogaine derivative, or pharmaceutically acceptable salt and/or solvate thereof and cannabinoid or pharmaceutically acceptable salt thereof. In some embodiments, the first tapered dose is given after the second, third, or a subsequent dose of compounds. The first tapered dose may be administered at any time after the previous dose of compounds. The first tapered dose can be given once, for example, followed by subsequent further tapered doses, or it can be given multiple times with or without subsequent, further tapered doses second, third, fourth, etc. tapered doses), which likewise can be given once or over multiple administrations, for example. In some embodiments, the first tapered dose is administered one hour, 6 hours, 12 hours, 18 hours, 24 hours, 36 hours, 48 hours, or more after the previous dose of compound. Similarly, second, third, fourth, etc. tapered doses, if given, can be given one hour, 6 hours, 12 hours, 18 hours, 24 hours, 36 hours, 48 hours, or more after the previous dose of compound.

In some embodiments, one tapered dose is given to achieve the desired lower therapeutic dose. In some embodiments, two tapered doses are given to achieve the desired lower therapeutic dose. In some embodiments, three tapered doses are given to achieve the desired lower therapeutic dose. In some embodiments, four or more tapered doses are Oven to achieve the desired lower therapeutic dose. Determination of the tapered doses, number of tapered doses, and the like can be readily made a qualified clinician.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms. In one embodiment, prolongation of the QT interval is equivalent to or less than the prolongation observed for methadone-treated patients.

In an embodiment, this invention relates to treatment or attenuation of acute or post-acute withdrawal from an addictive substance in an addicted patient with a maintenance amount of noribogaine, noribogaine derivative, or pharmaceutically acceptable salt and/or solvate thereof in combination with a cannabinoid or pharmaceutically acceptable salt thereof.

In some embodiments, the present invention is directed to a method to prevent relapse of substance abuse in an addicted patient treated to ameliorate said abuse, the method comprising periodically administering to said patient a maintenance dosage of noribogaine, noribogaine derivative, or pharmaceutically acceptable salt and/or solvate thereof in combination with a cannabinoid or pharmaceutically acceptable salt thereof.

In some embodiments, the patient undergoes long-term (e.g., one year or longer) treatment with maintenance doses of noribogaine, noribogaine derivative, or pharmaceutically acceptable salt and/or solvate thereof in combination with a cannabinoid or pharmaceutically acceptable salt thereof. In some embodiments, the patient is treated for acute withdrawal with therapeutic doses of noribogaine, noribogaine derivative, or pharmaceutically acceptable salt and/or solvate thereof and a cannabinoid or pharmaceutically acceptable salt thereof as described above, and then the amount of compound is reduced to maintenance levels after acute withdrawal symptoms have subsided or would be expected to have subsided. Acute withdrawal symptoms generally are the most pronounced in the first 48 to 72 hours after cessation of the drug of addiction, although acute withdrawal may last as long as a week or more.

In some embodiments, the patient is administered a high (therapeutic) dose of noribogaine, noribogaine derivative, or pharmaceutically acceptable salt and/or solvate thereof and a cannabinoid or pharmaceutically acceptable salt thereof for a period of time to ameliorate the most significant withdrawal symptoms, and then is administered a lower (maintenance) dose to prevent relapse to substance abuse. In some embodiments, the patient is administered a therapeutic dose of noribogaine, noribogaine derivative, or pharmaceutically acceptable salt and/or solvate thereof and a cannabinoid or pharmaceutically acceptable salt thereof for a period of time to ameliorate the most significant withdraw symptoms, and then is administered a decreasing (tapered) amount of the compound(s) over time until the maintenance dose is reached.

In some embodiments, the maintenance dose of noribogaine, noribogaine derivative, or pharmaceutically acceptable salt and/or solvate thereof and a cannabinoid or pharmaceutically acceptable salt thereof is about 10% to about 70% of the therapeutic dose.

In one embodiment, the therapeutic dose is tapered over time until the desired maintenance dose is reached. For example, in some embodiments, the first tapered dose is about 50% to about 95% of the therapeutic dose. In some embodiments, the second tapered dose is about 40% to about 90% of the therapeutic dose. In some embodiments, the third tapered dose is about 30% to about 85% of the therapeutic dose. In some embodiments, the fourth tapered dose is about 20% to about 80% of the therapeutic dose. The nature of the tapered dose will be a function of the patient's response to therapy over time. In some embodiments, the fifth tapered dose is about 10% to about 75% of the therapeutic dose. In some embodiments, one tapered dose is given to achieve the maintenance dose. In some embodiments, two tapered doses are given to achieve the maintenance dose. In some embodiments, three tapered doses are given to achieve the maintenance dose. In some embodiments, four or more tapered doses are given to achieve the maintenance dose. Determination of the tapered doses, number of tapered doses, and the like can be readily made a qualified clinician.

In some embodiments, the patient is administered periodically, such as once, twice, three time, four times, five times or six times daily with noribogaine, noribogaine derivative, or pharmaceutically acceptable salt and/or solvate thereof in combination with a cannabinoid or pharmaceutically acceptable salt. Noribogaine and cannabinoid may be administered to different times to maintain therapeutic and/or maintain levels of agent in the patient, but it is preferable to administer the noribogaine and cannabinoid at approximately the same time for patient compliance. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In a preferred embodiment, noribogaine and cannabinoid are administered orally, which may conveniently be provided in tablet, caplet, sublingual, liquid or capsule form. In certain embodiments, the compound(s) are provided as a pharmaceutically acceptable salt, for example noribogaine HCl, with dosages reported as the amount of free base compound. In some embodiments, the pharmaceutically acceptable salt and/or solvate is provided in hard gelatin capsules containing only the salt with no excipients.

Kits

One aspect of this invention is directed to a kit of parts for the treatment of substance abuse and/or symptoms of withdrawal in an addicted patient, wherein the kit comprises a single composition comprising noribogaine, noribogaine derivative, or pharmaceutically acceptable salt and/or solvate thereof and a cannabinoid or a pharmaceutically acceptable salt thereof or two compositions comprising each of the noribogaine and cannabinoid compositions and a means for administering the composition to a patient in need thereof. The means for administration to a patient can include, for example, any one or combination of noribogaine, noribogaine derivative, or pharmaceutically acceptable salt and/or solvate thereof and a cannabinoid or a pharmaceutically acceptable salt thereof, a transdermal patch, a syringe, a needle, an IV bag comprising the composition, a vial comprising the composition, an inhaler comprising the composition, etc. In one embodiment, the kit of parts further comprises instructions for dosing and/or administration of the composition.

In embodiments, the invention is directed to a kit of parts for administration of noribogaine, noribogaine derivative, or pharmaceutically acceptable salt and/or solvate thereof and a cannabinoid or a pharmaceutically acceptable salt thereof, the kit comprising multiple delivery vehicles, wherein each delivery vehicle contains a discrete amount of compound(s) and further wherein each delivery vehicle is identified by the amount of each compound provided therein; and optionally further comprising a dosing treatment schedule in a readable medium. In some embodiments, the dosing treatment schedule includes the amount of compound required to achieve each average serum level is provided. In some embodiments, the kit of parts includes a dosing treatment schedule that provides an attending clinician the ability to select a dosing regimen based on the sex of the patient, mass of the patient, compound, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of noribogaine, noribogaine derivative, or pharmaceutically acceptable salt and/or solvate thereof and a cannabinoid or a pharmaceutically acceptable salt thereof to a patient. Non-limiting, exemplary delivery vehicles include caplets, pills, capsules, tablets, powder, liquid, or any other form by which the drug can be administered. Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of noribogaine, noribogaine derivative, or pharmaceutically acceptable salt and/or solvate thereof and a cannabinoid or a pharmaceutically acceptable salt thereof, and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of compound recommended to be delivered will be within the dosages that result in the serum concentrations as provided herein.

In some embodiments, the kit of parts comprises multiple delivery vehicles in a variety of dosing options. For example, the kit of parts may comprise pills or tablets in multiple dosages, such as 60 mg, 30 mg, 25 mg. 20 mg, 15 mg, 10 mg, and/or 8 mg of noribogaine, noribogaine derivative, or pharmaceutically acceptable salt and/or solvate thereof per pill and multiple dosages of cannabinoid or pharmaceutically acceptable salt thereof ranging from less than 0.5 mg up to about 1 g depending on the cannabinoid to be administered. The noribogaine, noribogaine derivative, or pharmaceutically acceptable salt and/or solvate thereof and cannabinoid or pharmaceutically acceptable salt thereof may be delivered in separate dosage units. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

In embodiments, the unit dose form comprises one or multiple dosages to be administered periodically, such as once, twice, three times, four times, five times or six times daily with noribogaine, noribogaine derivative, or pharmaceutically acceptable salt and/or solvate thereof and a cannabinoid or pharmaceutically acceptable salt thereof. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician. In embodiments, the noribogaine, noribogaine derivative, or pharmaceutically acceptable salt and/or solvate thereof and the cannabinoid or pharmaceutically acceptable salt thereof are delivered at the same time, in the same dosage unit or at different times in separate dosage units.

In embodiments, dose ranges may be achieved by transdermal, oral, or parenteral administration of noribogaine, noribogaine derivative, or pharmaceutically acceptable salt and/or solvate thereof noribogaine, noribogaine derivative, or pharmaceutically acceptable salt and/or solvate thereof and a cannabinoid or pharmaceutically acceptable salt thereof in unit dose form. Such unit dose form may conveniently be provided in transdermal patch, tablet, caplet, liquid or capsule form. In certain embodiments, the noribogaine, noribogaine derivative, or pharmaceutically acceptable salt and/or solvate thereof is provided as noribogaine HCl, with dosages reported as the amount of free base noribogaine, noribogaine derivative, or pharmaceutically acceptable salt and/or solvate thereof. In some embodiments, the noribogaine HCl is provided in hard gelatin capsules containing only noribogaine HCl with no excipients and the cannabinoid or pharmaceutically acceptable salt thereof being provided in a separate dosage unit. In some embodiments, noribogaine, noribogaine derivative, or pharmaceutically acceptable salt and/or solvate thereof and the cannabinoid or pharmaceutically acceptable salt thereof is provided in saline for intravenous administration.

In another aspect, provided herein is a kit of parts for administration of noribogaine, noribogaine derivative, or pharmaceutically acceptable salt and/or solvate thereof and the cannabinoid or pharmaceutically acceptable salt thereof, the kit comprising multiple delivery vehicles, wherein each delivery vehicle contains a discrete amount of noribogaine and cannabinoid and further wherein each delivery vehicle is identified by the amount of noribogaine provided therein; and optionally further comprising a dosing treatment schedule in a readable medium.

In an embodiment, the amount of noribogaine, noribogaine derivative, or pharmaceutically acceptable salt and/or solvate thereof and cannabinoid or pharmaceutically acceptable salt thereof required to achieve each maximum serum level is provided in the readable medium. In another embodiment, the readable medium is a computer-readable medium. In another embodiment, the multiple delivery vehicles contain different amounts of noribogaine, noribogaine derivative, or pharmaceutically acceptable salt and/or solvate thereof and a cannabinoid or pharmaceutically acceptable salt thereof. In another embodiment, the dosing treatment schedule provides an attending clinician the ability to select a dosing regimen of noribogaine, noribogaine derivative, or pharmaceutically acceptable salt and/or solvate thereof and a cannabinoid or pharmaceutically acceptable salt thereof based on the sex of the patient, mass of the patient, and the serum level that the clinician desires to achieve. In another embodiment, the dosing treatment schedule further provides information corresponding to the volume of blood in a patient based upon weight and sex of the patient.

In embodiments, the present invention further relates to pharmaceutically acceptable formulations comprising a unit dose of noribogaine, noribogaine derivative, or pharmaceutically acceptable salt and/or solvate thereof and a cannabinoid or a pharmaceutically acceptable salt thereof, wherein the amount of compounds are sufficient to provide an effective dosage to effect a favorable therapeutic outcome without causing substantial side effects (e.g. by increasing QT interval) when administered to a patient.

In some embodiments, the unit dose of noribogaine, noribogaine derivative, or pharmaceutically acceptable salt and/or solvate thereof and a cannabinoid or a pharmaceutically acceptable salt thereof is administered in one or more dosings.

In some embodiments, the formulation is designed for periodic administration, such as once, twice, three time, four times, five times or six times daily with noribogaine, noribogaine derivative, or pharmaceutically acceptable salt and/or solvate thereof and a cannabinoid or a pharmaceutically acceptable salt thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the formulation designed for administration in accordance with the methods provide herein can be suitable for a variety of delivery modes including, without limitation, oral and transdermal delivery. Formulations suitable for internal, pulmonary, rectal, nasal, vaginal, lingual, intravenous, intra-arterial, intramuscular, intraperitoneal, intracutaneous and subcutaneous routes may also be used. Possible formulations include tablets, capsules, pills, powders, aerosols, suppositories, parenterals, and oral liquids, including suspensions, solutions and emulsions. Sustained release dosage forms may also be used. All formulations may be prepared using methods that are standard in the art (see e.g., Remington's Pharmaceutical Sciences, 16th ed., A. Oslo editor, Easton Pa. 1980).

In a preferred embodiment, the formulation is designed for oral administration, which may conveniently be provided in tablet, caplet, sublingual, liquid or capsule form.

Table: The following formulations exemplify preferred formulations of the present invention.

| Noribogaine | CBD (oil >99% | THC (oil 25% THC/0% CBD) |
|---|---|---|
| 30 mg | 0.25 ml | 0 |
| 30 mg | 0.5 ml | 0 |
| 30 mg | 1.0 ml | 0 |
| 30 mg | 0 | 0.25 ml |
| 30 mg | 0 | 0.5 ml |
| 30 mg | 0 | 1.0 ml |
| 30 mg | 0.5 ml | 0.25 ml |
| 30 mg | 0.5 ml | 0.5 ml |
| 30 mg | 0.5 ml | 1.0 ml |

* 1 ml of THC oil (99%) is 25 mg of THC.

The above combination of compounds may be formulated in unit dosage form in combination with pharmaceutically acceptable carriers, additives and/or excipients as otherwise described herein.

EXAMPLES

The inventors test the concept that low dose noribogaine in combination with a cannabinoid, especially a cannabinoid such as cannabidiol or tetrahydrocannabinoil (THC) may be used to synergistically favorably impact opioid withdrawal and reduce opioid tolerance in a subject or patient, especially a human subject or patient. First, the inventors measure the RNAs in microglia cells that are actively being translated to make protein (as indicators of the biological pathways that are activated in these cells during withdrawal). In addition, the inventors investigate mice given escalating doses of morphine followed by precipitated withdrawal and then use RiboTag, a new technology for retrieving the RNA from specific cell types, to interrogate the sequential changes occurring during microglial activation from opioid withdrawal. Second, the inventors assess whether the withdrawal syndrome can be prevented or attenuated by inhibiting microglial activation using engineered receptors to inhibit microglia during withdrawal. These experiments will utilize state of the art transgenic strategies that allow the inventors unprecedented precision in investigating and modulating microglia during acute opioid withdrawal. The ultimate goal of this proposal is to identify the impact that the inhibition of microglial activation and/or the anti-inflammatory activity of the cannabinoids in inhibiting inflammation of microglia has on the biological activity exhibited by noribogaine on withdrawal symptoms in the absence of cannabinoid coadministration. Molecular targets in microglia that can prevent the inflammation associated with withdrawal lead to the development of new treatments to mitigate opioid withdrawal, especially in combination with noribogaine. This will make withdrawal itself safer and potentially contribute to the motivation of addicted individuals to discontinue opioid use.

Microglial activation is an invariant feature of Alzheimer's disease (AD). It is noteworthy that cannabinoids are neuroprotective by preventing β-amyloid (Aβ-induced microglial activation both in vitro and in vivo. On the other hand, the phytocannabinoid cannabidiol (CBD) and tetrahydrocannabinol (THC) have shown anti-inflammatory properties in different paradigms. In addition, CBD, (R)-(+)-[2,3-dihydro-5-methyl-3-(4-morpholinylmethyl) pyrrolo-[1,2,3-d,e]-1,4-benzoxazin-6-yl]-1-naphthalenyl-methanone [WIN 55,212-2 (WIN)], a mixed CB(1)/CB(2) agonist, and 1,1-dimethylbutyl-1-deoxy-Δ(9)-tetrahydrocannabinol [JWH-133 (JWH], a CB(2)-selective agonist, concentration-dependently decreased ATP-induced (400 μM) increase in intracellular calcium ([Ca(2+)](i)) in cultured N13 microglial cells and in rat primary microglia. In contrast, 4-[4-(1,1-dimethylheptyl)-2,6-dimethoxyphenyl)]-6,6-dimethyl-bicyclo[3.1.1]hept-2-ene-2-methanol [HU-308 (HU)], another CB(2) agonist, was without effect. Cannabinoid and adenosine A(2A) receptors may be involved in the CBD action. CBD- and WIN-promoted primary microglia migration was blocked by CB(1) and/or CB(2) antagonists, JWH and HU-induced migration was blocked by a CB(2) antagonist only. All of the cannabinoids decreased lipopolysaccharide-induced nitrite generation, which was insensitive to cannabinoid antagonism. Finally, both CBD and WIN, after subchronic administration for 3 weeks, were able to prevent learning of a spatial navigation task and cytokine gene expression in β-amyloid-injected mice. CBD was able to modulate microglial cell function in vitro and induce beneficial effects in an in vivo model of AD. Given that CBD lacks psychoactivity, and provides anti-inflammatory activity directed to microglial activation and may induce apoptosis, the cannabinoids represent a novel therapeutic approach to the treatment of withdrawal symptoms with noribogaine.

The efficacy of noribogaine, noribogaine derivative, or a pharmaceutically acceptable salt and/or solvate thereof is evaluated in substance-dependent participants in a randomized, placebo-controlled, double-blind trial. Patients are administered between 8 and 30 mg of the compound(s) and the QT interval is measured. A favorable QT interval of 50 ms or less, preferably 40 ms or less is determined. The levels of noribogaine and cannabinoid are tested in vivo to determine the highest level of efficacy which can produce a QT interval at varying levels. Standard opioid withdrawal models are used to test noribogaine efficacy at low doses in combination with cannabinoid administration.

It is unexpectedly shown that noribogaine and a cannabinoid can produce favorable synergistic effects on opioid withdrawal symptoms in patients suffering from withdrawal symptoms or anticipating withdrawal symptoms by cessation of opioid analgesics. While not being limited by way of theory, it appears that noribogaine, because of its unique activity as a κ receptor agonist and μ receptor antagonist is able to reset the receptor interaction at the level of opioid behavioral symptoms of withdrawal after cessation of opioid agonist administration and this activity can be synergistically favorably impacted by the administration of at least one cannabinoid, preferably a cannabinoid with marked anti-inflammatory activity in microglia. It appears as if the anti-inflammatory cannabinoid synergistically favorably impacts the withdrawal behavioral symptomology by virtue of the microglial anti-inflammatory activity and this activity works in synergy with the receptor resetting of opiod withdrawal that occurs when noribogaine is coadministered with the cannabinoid. This finding is particularly unexpected given that this approach can be provided at very low dose levels of noribogaine and in light of the fact that the combination of morphine with naloxone produces fill withdrawal symptoms and a cannabinoid and naloxone precipitate withdrawal symptoms, in contradistinction to the present invention.

The invention claimed is:

1. A method of treating addiction to a chemical substance from which withdrawal symptoms occur after abstinence in a patient or subject in need thereof comprising co-administering to said patient or subject an effective amount of noribogaine, or a pharmaceutically acceptable salt, or ansolvate thereof, and cannabidiol (CBD).

2. The method according to claim 1, wherein said noribogaine, or the pharmaceutically acceptable salt, or ansolvate thereof is administered to said patient or subject in a daily amount ranging from 8 mg to 60 mg, and the CBD is administered to said patient or subject in an amount ranging from 0.5 mg to 1,000 mg.

3. The method according to claim 2, wherein said noribogaine, or the pharmaceutically acceptable salt, or ansolvate thereof, is administered to said patient or subject in a daily amount ranging from 10 mg to 30 mg.

4. The method according to claim 2, wherein the CBD is administered to said patient or subject in a daily amount of 1 mg to 800 mg.

5. The method according to claim 2, wherein the CBD is administered to said patient or subject in a daily amount of 50 mg to 800 mg.

6. The method according to claim 1, wherein said chemical substance from which withdrawal symptoms occur is an opiate or opioids, pain pills, stimulants, anxiety pills, hallucinogens or inhalants.

7. The method according to claim 1, wherein said chemical substance from which withdrawal symptoms occur is an opiate or opioid.

8. The method according to claim 1, wherein said chemical substance from which withdrawal symptoms occur is morphine, codeine, thebaine, heroin, nicomorphine, dipropanoylmorphine, desomorphine, methyldesorphine, acetylpropionylmorphine, dibenzoylmorphine, diacetyldihydromorphine, tramadol, oxycontin, hydrocodone, hydromorphone, tapentadol, meperidine, buprenorphine, fentanyl, methadone, codeine, diclofenac, ketorolac, etodolac, pregabalin, acetaminophen, ibuprofen, naproxen, celecoxib, hydroxyzine, lidocaine, amytriptylene, nortriptyline, duloxetine, clonidine, benzodiazepines, including diazepam and clonazepam, amphetamine, caffeine, ephedrine, MDMA, MDPV, DMT, PCP, mephedrone, methamphetamine, methylphenidate, cocaine, nicotine, phenylpropanolamine, propylhexedrine, pseudoephedrine, *Catha edulis* (Khat), alprazolam (Xanax), an aerosol product, a cleaning agent, a solvent or an adhesive.

9. The method according to claim 1, wherein noribogaine is administered to the patient or subject.

10. A method of claim 1, wherein the withdrawal symptom is anxiety.

* * * * *